(12) United States Patent
Yamamichi (10) Patent No.: US 7,348,185 B2
(45) Date of Patent: Mar. 25, 2008

(54) METHOD AND APPARATUS FOR CAPTURING TARGET SUBSTANCE

(75) Inventor: Junta Yamamichi, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 407 days.

(21) Appl. No.: 11/159,174

(22) Filed: Jun. 23, 2005

(65) Prior Publication Data
US 2005/0287577 A1    Dec. 29, 2005

(30) Foreign Application Priority Data
Jun. 25, 2004  (JP)  ............... 2004-188882

(51) Int. Cl.
*G01N 33/543* (2006.01)
*G01N 33/553* (2006.01)
(52) U.S. Cl. ............. 436/518; 436/526; 436/536; 436/538; 436/541
(58) Field of Classification Search ............. 436/518, 436/526, 536, 538, 541
See application file for complete search history.

(56) References Cited

U.S. PATENT DOCUMENTS

| | | | | |
|---|---|---|---|---|
| 4,108,976 A | * | 8/1978 | Reese .................... | 436/500 |
| 4,425,438 A | * | 1/1984 | Bauman et al. ........... | 436/527 |
| 4,793,973 A | * | 12/1988 | Ringrose ................. | 422/102 |
| 5,622,831 A | * | 4/1997 | Liberti et al. ............ | 435/7.21 |

FOREIGN PATENT DOCUMENTS

| | | |
|---|---|---|
| JP | 9-274032 | 10/1997 |
| JP | 2000-1565 | 1/2000 |
| JP | 2000-2705 | 1/2000 |

OTHER PUBLICATIONS

P.J. Halling et al., "Magnetic Supports for Immobilized Enzymes and Bioaffinity Adsorbents," 2 *Enzyme Microb. Technol.* 2-10 (Jan. 1980).

* cited by examiner

*Primary Examiner*—Christopher L. Chin
(74) *Attorney, Agent, or Firm*—Fizpatrick, Cella, Harper & Scinto

(57) ABSTRACT

A method for capturing a target substance in a sample, comprising the steps of preparing particles capable of capturing the target substance in a dispersed state in a fluid, aggregating the particles, and allowing the particles to capture the target substance in the sample by bringing the sample into contact with the particles aggregated.

6 Claims, 7 Drawing Sheets

METHOD AND APPARATUS FOR CAPTURING TARGET SUBSTANCE

BACKGROUND OF THE INVENTION

1. Field of the Invention

The present invention relates to a method for capturing a target substance by means of fine magnetic particles and an apparatus using the method.

2. Related Background Art

In a sensor for detecting a biological substance such as a protein and a nucleic acid as well as a chemical substance such as a gas, the surface area of a reaction site is a critical factor for controlling a detection sensitivity and a reaction rate. An increase in surface area leads to an improvement in the performance of a sensor. Up to now, methods using a porous material as a base have been proposed for holding a large amount of reactive substance capable of reacting with a detection target. Such known methods for improving the performance of a sensor employ a microfilter formed of a nitrocellulose film or a nylon film, paper, nonwoven cloth and thread as a base. A porous material, since it has a substantial surface area a thousand times to ten thousand times as large as an apparent surface area, can immobilize or carry a large amount of component capable of capturing a target substance on the surface. Japanese Patent Application Laid-Open Nos. 2000-1565 and 2000-2705 disclose a method of manufacturing a porous surface body. Furthermore, Japanese Patent Application Laid-Open No. H9-274032 proposes a miniaturized high sensitive monitoring system for nitrogen dioxide concentration using a porous body.

However, when the surface area of a porous body is increased to detect a trace of constituents selectively or to increase the sensitivity, it is usually not easy to wash efficiently the entire porous body during a washing step carried out after a capturing reaction. In removing a non-target substance and the like, which are substances other than a target substance, by washing, if the amount of such a non-target substance remaining in a porous body is negligibly small compared to that of a target substance, no problem arises; however, if the amount of a target substance in a sample is extremely small, such a substance which affects detection of a target substance, must be washed off in a high removal rate. Furthermore, when a porous body having a flow resistance within a practical range of value is placed in a microchannel, the porous body itself acts as a light scatterer. Therefore, such a porous body is sometimes not suitable for optical detection. On the other hand, a porous material used in a gas sensor has very small pores whose diameters are of the order of nanometers. Such a porous body has problems in permeability and reactivity when used in a solution system, and in flow resistance when used in a microchannel.

SUMMARY OF THE INVENTION

The present invention has been made in view of the background art and provides a method and apparatus for capturing a target substance improved in efficiency of a capturing reaction by forming a porous body which consists of a particle aggregate capable of capturing the target substance through a reaction, thereby increasing an apparent surface area of a reaction site, and reducing the diffusion length of the target substance. The present invention also employs particles capable of producing a reversible aggregate. Therefore, after the reaction between a particle aggregate and a sample, the particle aggregate can be redispersed, so that the redispersed particles can be subjected to other steps such as detecting and collecting a captured target substance.

According to the present invention, there is provided a method for capturing a target substance in a sample, comprising the steps of:

preparing particles capable of capturing the target substance in a dispersed state in a fluid, aggregating the particles, and allowing the particles to capture the target substance in the sample by bringing the sample into contact with the aggregated particles.

According to the present invention, there is provided an apparatus for capturing a target substance in a sample, comprising a flow channel for delivering the sample, particles immobilized in the flow channel and capable of capturing the target substance, aggregation means for aggregating the particles in the flow channel, and delivery means for delivering the sample through the flow channel.

The present invention provides a method for capturing a target substance by introducing fine particles capable of capturing the target substance into a flow channel, aggregating the fine particles in a desired region in the flow channel, introducing a sample into the flow channel, and allowing the fine particles to react with the target substance of the sample. Since the fine particle aggregate can be redispersed after the capturing reaction, the particles can be subjected to other steps such as detection and collection steps.

DESCRIPTION OF THE PREFERRED EMBODIMENTS

The present invention will be explained in more detail by way of Embodiments. A method for capturing a target substance in a sample according to this Embodiment comprises the steps of introducing particles capable of capturing a target substance into a flow channel; aggregating the particles to form an aggregate in a desired region (capturing reaction region) in the flow channel and holding the aggregate in the region; and introducing a sample in the flow channel and permitting the particles to capture the target substance in a sample. Furthermore, the method may comprise at least one of post steps of washing the particles and detecting the target substance.

As a medium for delivering particles through a flow channel, a liquid or a gas can be used, which makes it possible to perform operations of delivering, aggregating, and detecting particles according to the present invention. The diameters of particles preferably fall within the range of 0.02 to 20 μm, and more preferably, in the range of 1.0 to 20 μm. Treatment for preventing mutual bonding and adhesion of particles may be applied to the surface of particles. As the surface treatment, BSA, PEG (polyethylene glycol), or casein may be applied onto the surface. In a detection step, the medium for delivering particles through a flow channel may be in motion or not in motion.

Note that detection of a target substance may not be performed in the form of an aggregate but performed after the aggregate is redispersed into particles in a subsequent step and, if necessary, washed. Furthermore, since this method has post steps for redispersing and collecting particles, a captured target substance and particles can be collected and used in detection and other usage. As the particles for capturing a target substance, fine magnetic particles are preferably used. The aggregation step is preferably performed by externally applying a magnetic field.

On the other hand, the apparatus according to this Embodiment is one for capturing a target substance in a sample and characterized by comprising means for introducing particles capable of capturing the target substance into a flow channel; means for aggregating the particles in a desired region (capturing reaction region) in the flow channel; means for introducing the sample after the particles are aggregated, thereby allowing the particle aggregate to capture the target substance in the sample. The apparatus may have washing means for use in a washing step. Furthermore, the apparatus for capturing a target substance according to this Embodiment of the present invention may have means for detecting a target substance. The detection means may not detect the target substance from an aggregate but detect the target substance from particles redispersed from the aggregate. In this case, the apparatus has means for redispersing particles. In the apparatus according to the Embodiment of the present invention, addition of a redispersion means and a collection means to the apparatus makes it possible to provide a constitution of collecting the captured target substance and particles and desirably subjecting them to detection and separation steps. Note that in this apparatus, fine magnetic particles are preferably used as the particles. As the aggregation means, means for externally applying a magnetic field is preferably used.

Now, the method and apparatus for capturing a target substance according to the present invention using fine magnetic particles will be explained below by way of the accompanying drawings. A general structure of an apparatus for use in the method for capturing a target substance according to the present invention is preferably a microflow chip represented by FIG. 1. 1, 2, 3, 4, 101 and 102 represent base (substrate), inlet, flow channel, outlet, fine particle aggregation region and detection region respectively in FIG. 1. Naturally, a capillary or the like other than a microflow chip may be used. In FIG. 2, a detection section 5 and an aggregation means. 6 are arranged at the same position relative to a flow channel 3. In this case, the aggregation means 6 is preferably a magnetic field generating means such as a permanent magnet and an electromagnet. The detection section 5 preferably has an optical detection element such as a photo multiplier or CCD.

Figure 1:
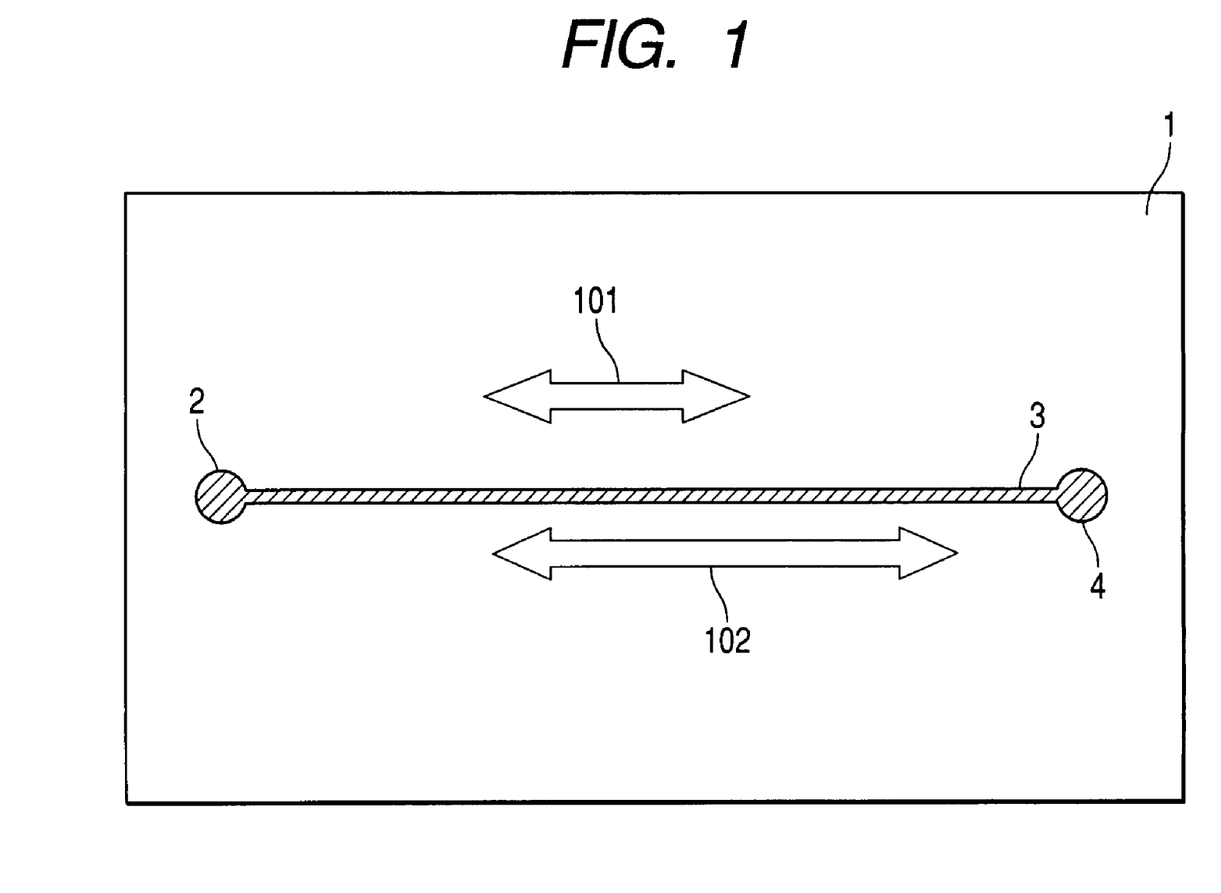
FIG. 1 is a schematic illustration showing a method and apparatus for capturing a target substance according to the present invention.
Figure 2:
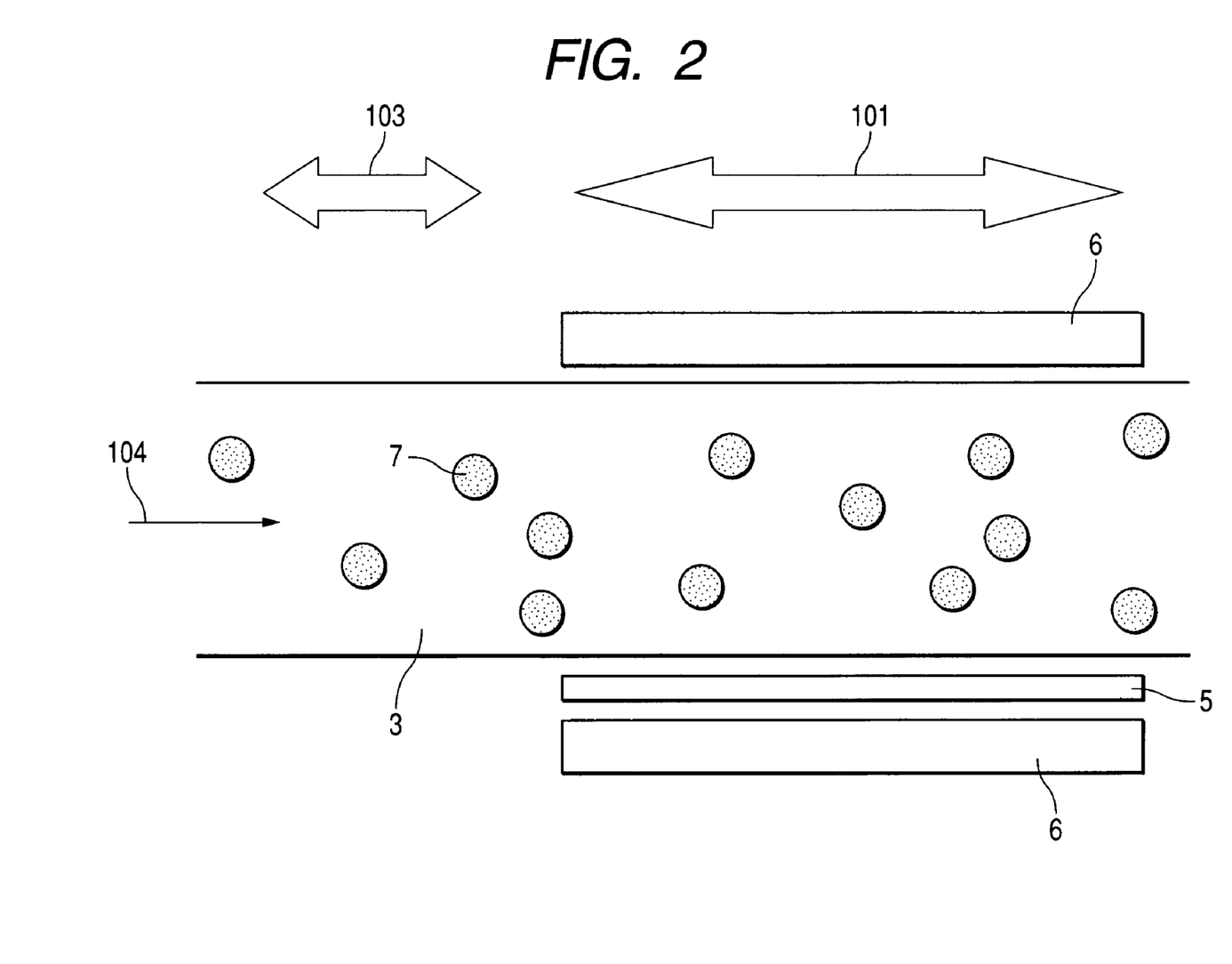
FIG. 2 is a schematic illustration showing a profile of the flow channel of FIG. 1.

A deliver solution containing fine magnetic particles 7 is introduced into the flow channel 3 though an inlet 2 provided in a substrate shown in FIG. 1 and fed through the flow channel 3 by a delivery means having a syringe pump (not shown) or the like. FIG. 2 shows the state where the aggregation means 6 does not function. Note that the delivery means having a syringe pump or the like serves as a fine magnetic particle introduction means as well as a sample delivery means. 3, 101, 103 and 104 represent flow channel, supply of a fluid, introduction region and fine particle aggregation region respectively in FIG. 2.

Figure 3:
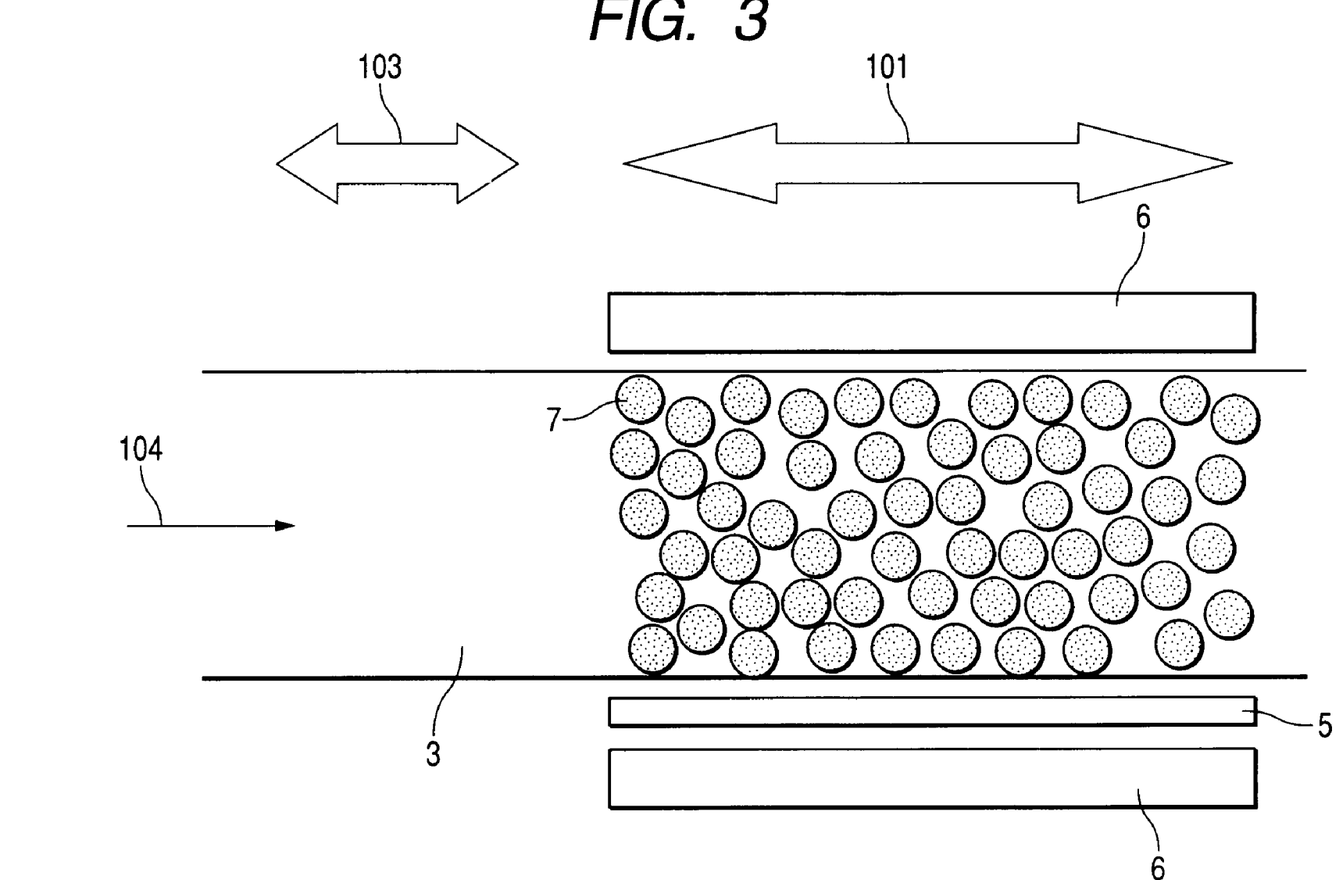
FIG. 3 is a schematic illustration showing the particle aggregation section of FIG. 1.

In this Embodiment, when the aggregation means 6 for aggregating particles by application of a magnetic field is functioned, the fine magnetic particles 7 aggregate to form an aggregate in a fine particle aggregation region 101 where a capturing reaction is performed, as is schematically shown in FIG. 3. 3, 5, 103 and 104 represent flow channel, detection region, introduction region and supply of a fluid respectively in FIG. 3. The aggregate acts similarly to a porous body. Taking supply of a fluid into consideration, the aggregate preferably has voids in the order of micrometers. Naturally, the size and ratio of the voids can be controlled by diameters of fine particles and degree of aggregation. The degree of aggregation can be adjusted by the strength of the externally applied magnetic field and the magnetic properties of the fine magnetic particles in combination. Furthermore, if efficiency of a capturing reaction is improved by adjusting the aggregation density and washing performance is controlled to a satisfactory level, the efficiency of capturing a target substance and detection sensitivity can be improved. More specifically, the particles for capturing a target substance according to the present invention, represented by fine magnetic particles in the aforementioned case, are capable of forming an aggregate and redispersing from an aggregation state into an original dispersion state, in other words, capable of forming a reversible aggregate. The aggregate of particles formed in the region for capturing reaction has a density (referred to as an "aggregation state") required for an effective reaction with a target substance in a sample. In the case where fine magnetic particles are used, the aggregation state can be controlled by the strength of a magnetic field.

Any one of the fine magnetic particles shown below may be used. The material for such fine magnetic particles is not particularly limited and, for example, include Ni particles and composite particles formed of polymer (nylon, polyacrylamide, polystyrene, etc.) and ferrite such as metaliron, $Fe_3O_4$, $\gamma$-$Fe_2O_3$, Co-$\gamma$-$Fe_2O_3$, $(NiCuZn)O.(CuZn)O.Fe_2O_3$, $(MnZn)O.Fe_2O_3$, $(NiZn)O.Fe_2O_3$, $SrO.6Fe_2O_3$, $BaO.6Fe_2O_3$, and $Fe_3O_4$ (particle diameter 200 Å) coated with $SiO_2$ (see Enzyme Microb. Technol., vol. 2, p. 2-10 (1980)).

Figure 4A:
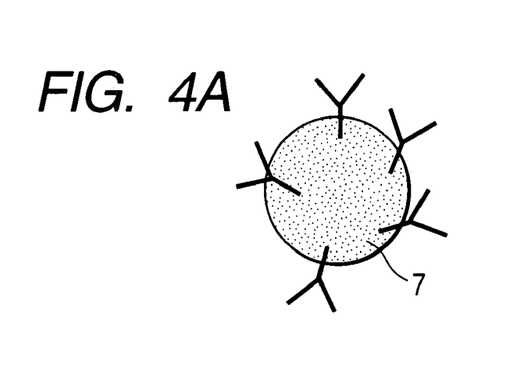
FIGS. 4A, 4B and 4C include illustrations showing the structure of fine particles according to the present invention.
Figure 4B:
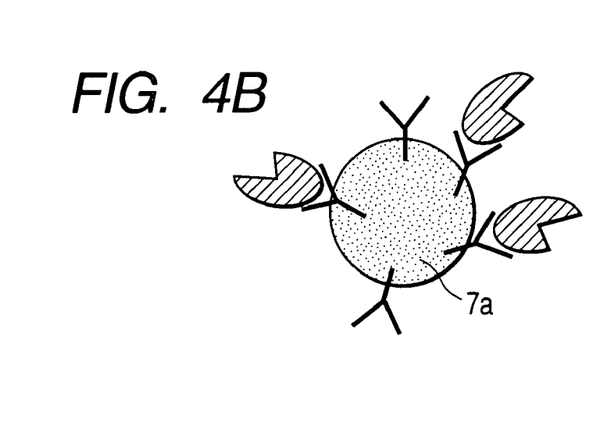

In the state shown in FIG. 3, fine particles are trapped as aggregate in the fine particle aggregation region 101 and a deliver solution flows through the aggregate. A capturing substance such as an antibody for specifically capturing a target substance is immobilized on the surface of the fine particles, as shown in FIG. 4A. Therefore, the aggregate can be used as a functional porous body capable of specifically capturing a target substance. Each of the fine particles reacts with a target substance 9 in the sample solution and specifically captures the target substance 9 possibly with the help of a capturing substance 8 immobilized on the surface of the fine particle 7, as shown in FIG. 4B. Naturally, such a porous body can be used for detecting, separating and removing a specific substance from a target solution.

Figure 4C:
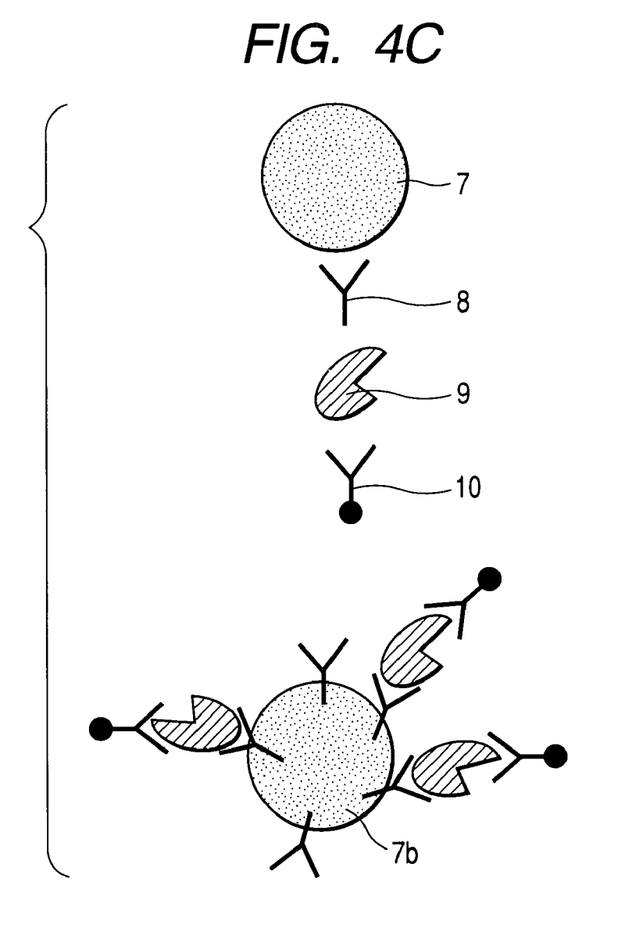

When an optically detectable label is used, a secondary antibody (labeled antibody) 10 capable of specifically recognizing the target substance 9 may be used as shown in FIG. 4C. The target substance can be detected by an enzyme-labeled antibody in combination with an electrode or a fluorescence-labeled antibody and a chemical luminescence-labeled antibody in combination with an optical detection system. Examples of enzymatic labeling substances include glucose oxidase, choline oxidase, and lactose oxidase. Examples of fluorescent labeling substances include 5-carboxyfluoresceine, Quene-1(8-amino-2-(trans-2-aminostyryl)-6-methoxyquinoline-N,N,N'N'-tetracetate, tetrasodium salt), 2',7'-bis (2-Carboxyethyl)-5 (6)-Carboxyfluorescein (BCECF), and rhodamine. As a chemical luminescence labeling substances, horseradish peroxidase and the like may be mentioned. The fine particles tagged with a specific label may be subjected to detection as they are maintained in the aggregate state or after the fine particles are redispersed from the aggregate by releasing the aggregation means. The detecting region may be overlapped with the aggregation region or located downstream of the flow channel. Furthermore, when no optical detection means is used, it is not necessary to redisperse the aggregate since optical scattering has no effect upon the detection. Moreover, after the fine particles are redispersed and then sufficiently washed in a discretely arranged washing region, detection can be made by a detection means. Note that 7 in FIG. 4A, 7a in FIG. 4B and 7b in FIG. 4C represent fine particles capable of specifically capturing target substance, fine particles that have specifically captured target and fine particles capturing target substance specifically labeled respectively.

A detection target substance is preferably recognized specifically by an antibody such as a biological substance (protein, nucleic acid, sugar chain), allergen, bacteria, or virus, and forms a complex with magnetic particles. Preferable examples of such a detection target substance include disease-associated proteins such as α-fetoprotein (AFP), basic fetoprotein (BFP), prostate specific antigen (PSA), prostate acidic phosphatase (PAP), cancer embryonic antigen (CEA), BCA225, and immunosuppression acidic protein (IAP). When these substances are used as target substances, specific antibodies against them can be used as capturing substances.

On the other hand, when the apparatus according to the present invention is used as a separation/removal apparatus, the fine particles are maintained in an aggregation state and used as a filter for specifically removing a substance. Alternatively, after the particles of an aggregate are redispersed by releasing the aggregation means, fine particles capturing a target substance may be collected.

According to the method and apparatus for capturing a target substance according to the present invention, fine particles capable of capturing a target substance through a reaction are aggregated to form a porous body. By increasing an apparent reaction surface area and reducing the diffusion length of a target substance, efficiency of capturing the target substance through a reaction can be increased. Furthermore, after the reaction, the fine particle aggregate can be redispersed by releasing the application of a magnetic field and therefore can be subjected to other steps such as a detection step and a collection step for a captured substance.

The particles for capturing a target substance according to the present invention are those, as represented by fine magnetic particles, capable of aggregating and redispersing into an original dispersion state, that is, capable of forming a reversible aggregate. The aggregate formed in a capturing reaction region has a particle density (i.e., aggregation state) required for efficiently reacting with a target substance in a sample. When fine magnetic particles are used, such an aggregation state can be controlled by the strength of a magnetic field.

EXAMPLES

The present invention will now be explained in more detail by way of Examples, which will not be construed as limiting the present invention.

Example 1

Figure 5:
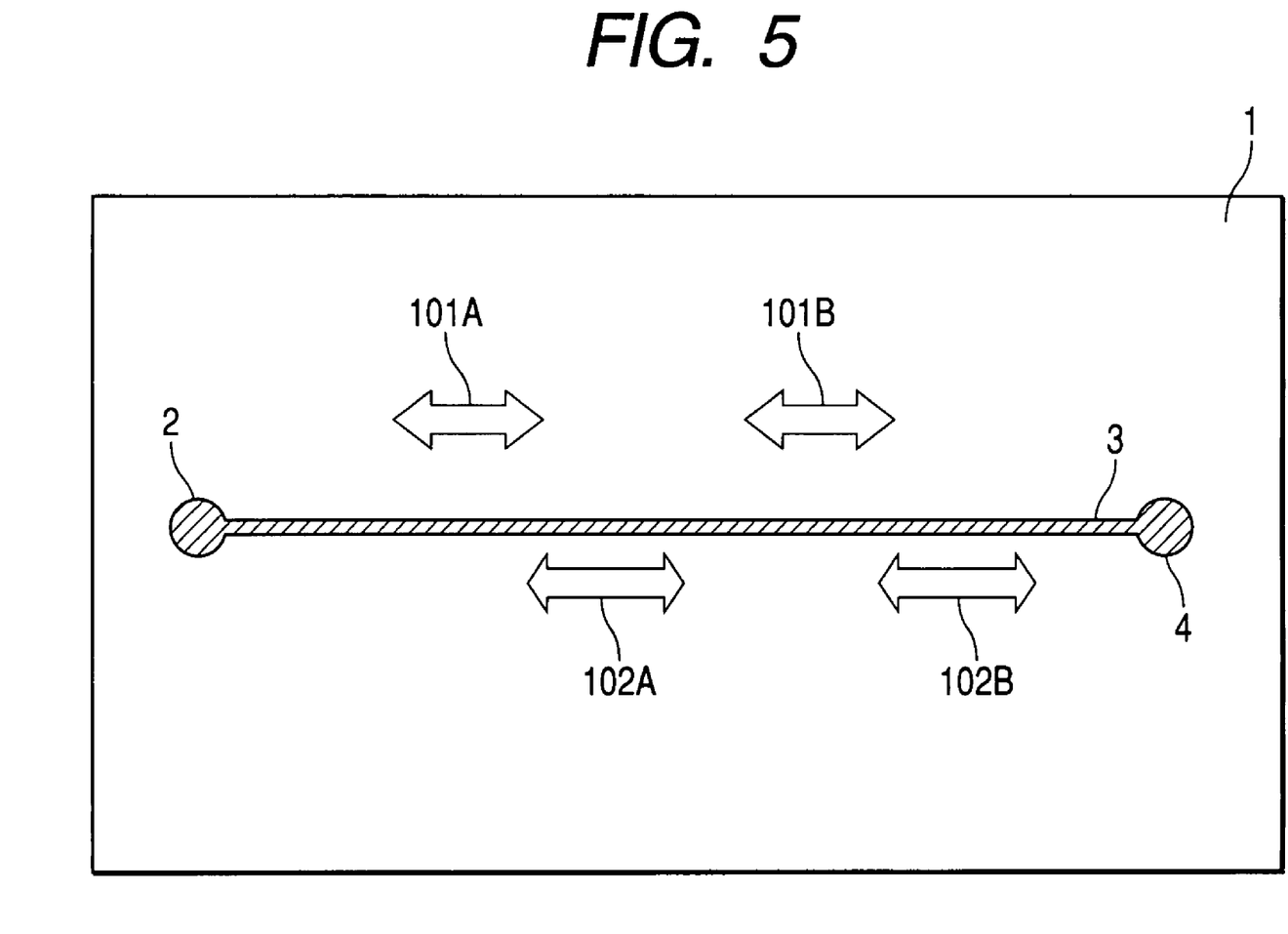
FIG. 5 is a schematic illustration showing Example 1.

FIG. 5 is a schematic view for illustrating a method for capturing a target substance according to Example 1 of the present invention. The target substance capturing apparatus of FIG. 5 is formed of a base (substrate) 1, a flow channel 3, an inlet 2 for introducing a deliver solution containing fine particles and a target substance into the flow channel 3, and an outlet 4 for discharging the deliver solution (from which the fine particles and the target substance have been delivered) from the flow channel 3. Between the inlet 2 and the outlet 4, a plurality of fine particle aggregation regions 101A, 101B and detection regions 102A, 102B are arranged.

The capturing apparatus of FIG. 5 employs a composite substrate 1, which is formed by adhering a polydimethyl siloxane (PDMS) resin substrate and a glass substrate to each other. The flow channel 3 of 100 µm width and 50 µm depth is formed by removing a predetermined portion from the PDMS substrate by a molding method using a thick-film photosensitive resin template, which has a microstructure photographically formed on a silicon substrate. Thereafter, the opening of the groove of the flow channel 3 is covered by adhering a flat glass plate thereto. A deliver solution and a target substance are introduced through the inlet 2 into the flow channel 3 by use of a syringe pump or the like.

As fine magnetic particles for forming an aggregate, Micromer-M (10 µm in diameter) manufactured by a company Micromod (Germany) is used. The particles are formed by coating the surface of commercially available fine superparamagnetism particles with protein A. By virtue of protein A, which can specifically bind to the Fc region of IgG antibody, any antibody can be immobilized. Examples of a target substance used herein include human α-fetoprotein (AFP) and human basic fetoprotein (BFP) dissolved in a phosphate buffer solution. An anti-human AFP polyclonal antibody derived from a rabbit and an anti-human BFP polyclonal antibody derived from a rabbit each is immobilized on the corresponding fine magnetic particles.

Figure 6:
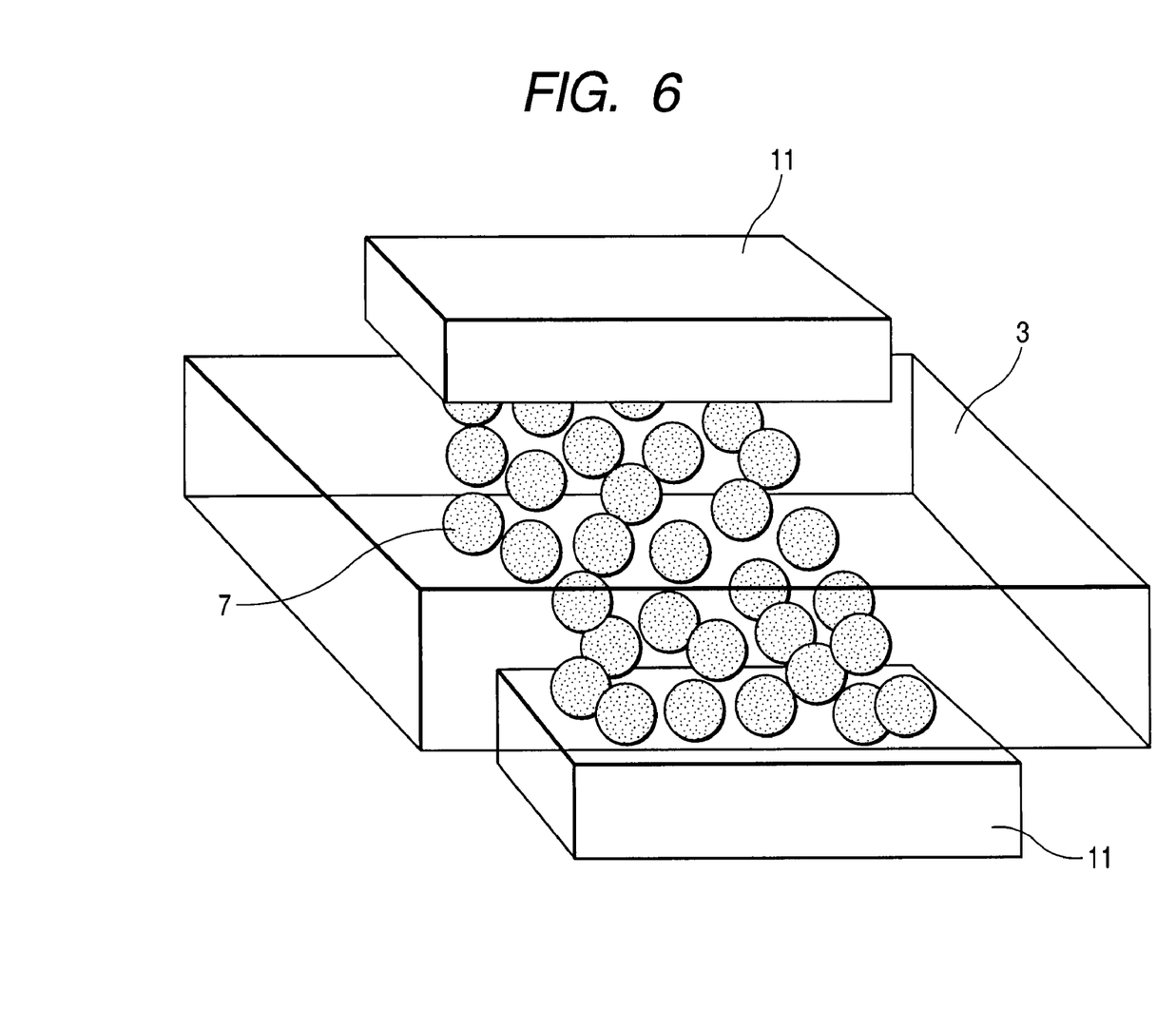
FIG. 6 is a schematic illustration showing a fine particle aggregation section according to Example 1.

In this Example, two types of detection target substances are used. First, fine magnetic particles modified with the anti-human AFP antibody, which form an aggregate in aggregation region 101B, are introduced through the inlet 2 so as not to aggregate in aggregation region 101A (for example, by applying no magnetic field to aggregation region 101A). In this case, an aggregate of the fine magnetic particles modified with the anti-human AFP antibody is formed in aggregation region 101B by a magnet 11 provided in region 101B, as shown in FIG. 6. 3 and 7 in FIG. 6 represent microchannel and fine particles respectively. While holding the aggregate, fine magnetic particles modified with the anti-human BFP antibody, which form an aggregate in aggregation region A, are introduced through the inlet 2 and an aggregate of the fine magnetic particles modified with the anti-human BFP antibody is formed in the same manner as in aggregation region 101A.

The phosphate buffer solution containing human AFP and human BFP serving as detection target substances is introduced through the inlet 2 to allow the target substances to be specifically captured in aggregation section B and A. Thereafter, a phosphate buffer is supplied to wash off substances (non-specific binding substance) remaining in the flow channel. Furthermore, 5-caroboxyfluorosceine labeled anti-human AFP antibody and rhodamine labeled anti-human BFP antibody, each independently binds specifically to detection target substances are introduced through the inlet 2 to label fluorescently fine magnetic particles capturing detection target substances. Similarly, a phosphate buffer solution is supplied to wash off substances (non-specific binding substance) remaining in the flow channel.

Figure 7:
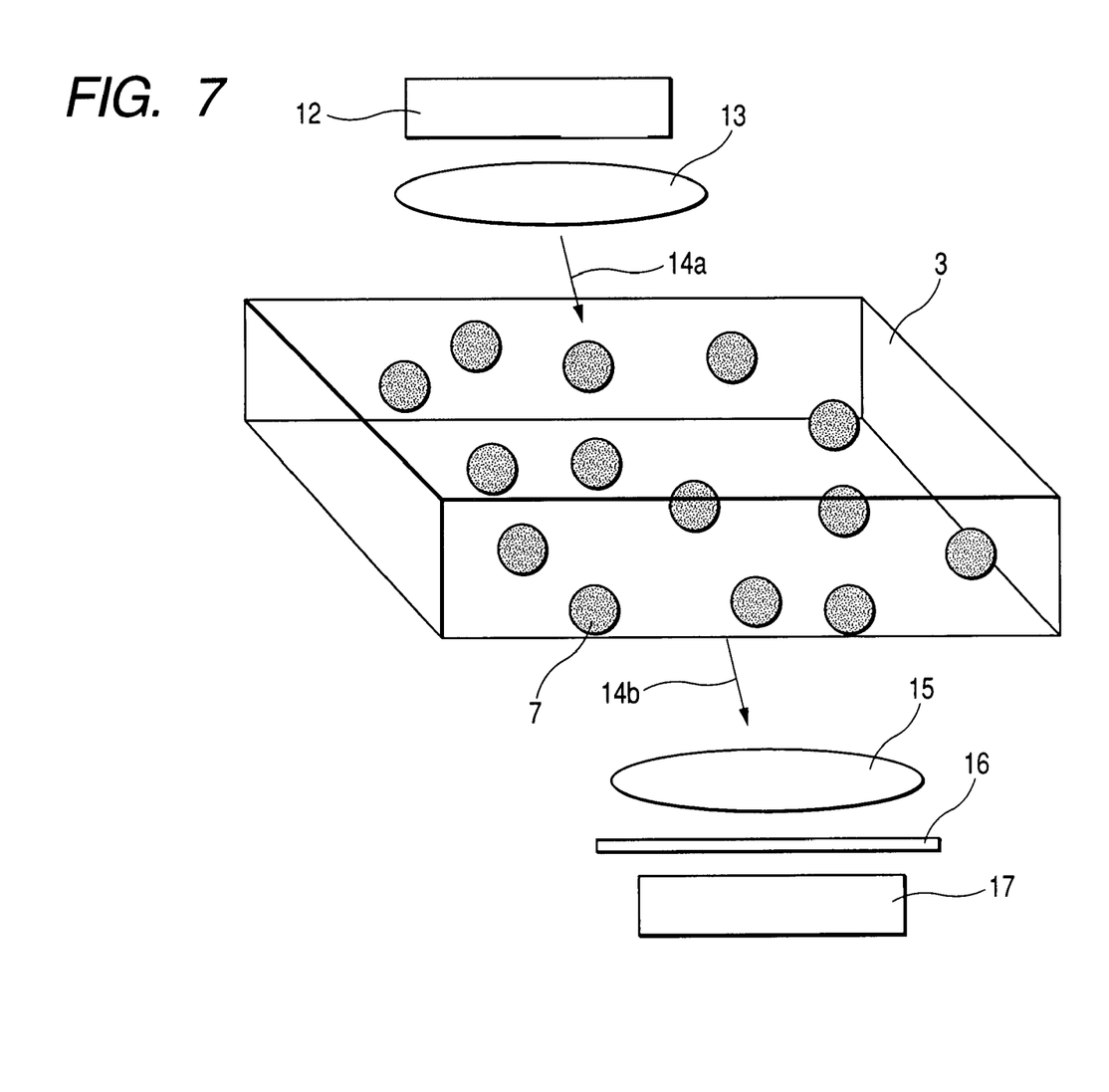
FIG. 7 is a schematic illustration showing a detection section according to Example 1.

The target substance captured is detected as follows. A detection system as shown in FIG. 7 is constructed in detection regions 102A and 102B. 3, 7, 12, 13, 14a, 14b, 15, 16 and 17 represent microchannel, fine particles, laser diode, collimator lens, parallel incident light, transmission light, collimator lens, filter, and photomultiplier in FIG. 7. These detection sections are irradiated with laser light via a glass cover to allow fluorescent light to emit from the labels. The intensity of the fluorescent light thus emitted is measured by a photomultiplier 17 through a base 1. Based on a calibration curve previously prepared by using target substances known in concentration, the amounts of the target substances, human AFP and human BFP, are determined. Prior to the detection, fine magnetic particles are redispersed by removing the magnetic field from the aggregation regions while supplying a phosphate buffer solution and sent to the detection regions. Naturally, it is practically preferable to perform detection operation first at the aggregation region 101B and detection region 102B located downstream.

Example 2

In the same manner as in Example 1, a target substance is specifically captured in a fine particle aggregation section in a flow channel. This Example is directed to removing viruses contained in a target solution. An antibody specifically binding to adenovirus is immobilized on the surface of fine magnetic particles. Adenovirus is captured by the resultant fine magnetic particles in fine particle aggregation region, thereby removing adenovirus from the target solution. The fine magnetic particles capturing adenovirus are redispersed by removing a magnetic field from the aggregation region while supplying a phosphate buffer from the inlet 2, simultaneously. In this way, the particles can be collected from the outlet 4.

This application claims priority from Japanese Patent Application No. 2004-188882 filed on Jun. 25, 2004, which is hereby incorporated by reference herein.

What is claimed is:

1. A method for capturing a target substance in a sample, comprising the steps of:
    preparing particles capable of capturing the target substance in a dispersed state in a fluid,
    aggregating the particles, and
    allowing the particles to capture the target substance in the sample by bringing the sample into contact with the particles aggregated.

2. The method for capturing a target substance according to claim 1, further comprising a step of removing a substance remaining uncaptured after the capturing step.

3. The method for capturing a target substance according to claim 1, further comprising a step of detecting the target substance captured by the particles.

4. The method for capturing a target substance according to claim 1, further comprising a step of redispersing the particles followed by detecting the target substance captured by the particles after the capturing step.

5. The method for capturing a target substance according to claim 1, further comprising a step of redispersing the particles in a fluid followed by collecting the particles.

6. The method for capturing a target substance according to claim 1, wherein the particles have magnetic properties and the particles are aggregated by externally applying a magnetic field.

* * * * *

UNITED STATES PATENT AND TRADEMARK OFFICE
CERTIFICATE OF CORRECTION

| | | |
|---|---|---|
| PATENT NO. | : 7,348,185 B2 | Page 1 of 1 |
| APPLICATION NO. | : 11/159174 | |
| DATED | : March 25, 2008 | |
| INVENTOR(S) | : Junta Yamamichi | |

It is certified that error appears in the above-identified patent and that said Letters Patent is hereby corrected as shown below:

COLUMN 1:

Line 44, "in" should read --at--.

COLUMN 2:

Line 16, "comprising" should read --comprising:--.

COLUMN 4:

Line 42, "include" should read --includes--.

COLUMN 7:

Line 26, "by-remov-" should read --by remov- --.

Signed and Sealed this

Second Day of September, 2008

JON W. DUDAS
*Director of the United States Patent and Trademark Office*